(12) United States Patent
Leshem et al.

(10) Patent No.: US 6,215,893 B1
(45) Date of Patent: Apr. 10, 2001

(54) APPARATUS AND METHOD FOR MEASUREMENT AND TEMPORAL COMPARISON OF SKIN SURFACE IMAGES

(75) Inventors: Ze'ev Leshem, Maccabim; Tuvia Kutscher, Shoham, both of (IL)

(73) Assignee: Romedix Ltd., Rehovot (IL)

( * ) Notice: Subject to any disclaimer, the term of this patent is extended or adjusted under 35 U.S.C. 154(b) by 0 days.

(21) Appl. No.: 09/137,513

(22) Filed: Aug. 20, 1998

(30) Foreign Application Priority Data

May 24, 1998 (IL) .......................................... 124616

(51) Int. Cl.$^7$ ...................................................... G06K 9/00
(52) U.S. Cl. .......................... 382/128; 382/165; 382/164
(58) Field of Search .................................... 382/115, 128, 382/108, 173, 168, 171, 162, 165, 131, 132, 164, 225

(56) References Cited

U.S. PATENT DOCUMENTS

| | | | |
|---|---|---|---|
| 5,815,591 | * | 9/1998 | Gaborski .............................. 382/130 |
| 6,018,590 | * | 9/1998 | Gaborski .............................. 382/168 |

OTHER PUBLICATIONS

Lee et al. "A Multi Stage Segmentation Method for Images of Skin Lesions." Proceedings. IEEE Pacific Rim conference on Communications, computers, and Signal Processing, 1995. pp. 602–605, May 1995.*

Schmid et al. "Colour segmentation for the analysis of pigmented skin lesions." Sixth International conference on Image Processing and Its Applications, 1997. vol. 2. pp. 668–692, Jul. 1997.*

* cited by examiner

*Primary Examiner*—Bhavesh Mehta
(74) *Attorney, Agent, or Firm*—Edward Langer, Pat. Atty.

(57) ABSTRACT

Apparatus and method for temporal comparison of skin surface images which is fully automatic and based on robust parameters, using a CCD camera provided with telecentric optics to enabling the capture of images with constant magnification independent of the camera-object distance. The camera is linked to a PC with a frame grabber for storing the image and processing means for calibrating light and for calculating statistics of the image. The illumination source provides a homogeneous illumination of the skin, and the light is calibrated by transforming an acquired image into the model image which would have resulted if illumination of the object were solely by the reference (white) light. Three monochromatic images are produced, one for each of three color channels. The three images are grabbed and processed, and a combination of these three images gives the true color (red, green and blue or RGB) image. An algorithm uses the image and reference image to calculate the skin/lesion border which the eye would suggest if the lesion was illuminated by a standard white light. The image is processed to give the contour of the lesion, and statistics are extracted to score the necessary parameters (metrics). Therefore, the physician is provided with various metrics in a more reliable fashion than could be done manually and these are displayed together with the images obtained at various times. The images can be examined for visual changes over time and for quantitative change in the metrics over time, providing a comprehensive solution to the problems encountered in previous lesion tracking systems. The system assists the physician in the decision making process of malignancy determination. The features are extracted in a manner which is fairly immune to noise, i.e. robust, thus leading to a high repeatability and reliability of the system. The features extracted have a high correlation with the malignancy of the lesion enabling the physician to make a decision regarding the type of lesion with high specificity and sensitivity.

16 Claims, 8 Drawing Sheets

Matrix_XYZitu_TO_RGB[0][0]=3.0630;
Matrix_XYZitu_TO_RGB[0][1]=-1.3933;
Matrix_XYZitu_TO_RGB[0][2]=-0.4757;
Matrix_XYZitu_TO_RGB[1][0]=-0.0969;
Matrix_XYZitu_TO_RGB[1][1]=1.8758;
Matrix_XYZitu_TO_RGB[1][2]=0.0416;
Matrix_XYZitu_TO_RGB[2][0]=0.0678;
Matrix_XYZitu_TO_RGB[2][1]=-0.2289;
Matrix_XYZitu_TO_RGB[2][2]=1.0692;

Matrix_RGB_TO_XYZitu [0][0]=0.4306;
Matrix_RGB_TO_XYZitu [0][1]=0.3416;
Matrix_RGB_TO_XYZitu [0][2]=0.1783;
Matrix_RGB_TO_XYZitu [1][0]=0.2220;
Matrix_RGB_TO_XYZitu [1][1]=0.7067;
Matrix_RGB_TO_XYZitu [1][2]=0.0713;
Matrix_RGB_TO_XYZitu [2][0]=0.0202;
Matrix_RGB_TO_XYZitu [2][1]=0.1296;
Matrix_RGB_TO_XYZitu [2][2]=0.9392;

APPARATUS AND METHOD FOR MEASUREMENT AND TEMPORAL COMPARISON OF SKIN SURFACE IMAGES

FIELD OF THE INVENTION

The present invention relates to medical equipment and methods, and more particularly to an apparatus and a method for measurement and temporal comparison of skin surface images.

BACKGROUND OF THE INVENTION

The current rise in skin cancer incidence and the increased public awareness of the dangers of skin cancer has reinforced a need for tracking of skin lesions in a reliable and accurate fashion. Most important is the need for a method of early detection of melanoma, the deadliest skin cancer. Until recently, when a physician noted a lesion on a patient the method of recording was through painstaking notes and measurements. However, this is not necessarily an objective nor sufficiently stringent method of follow-up and may be insufficient for accurate diagnosis.

In order to standardize the notetaking procedure, the clinical ABCD system for checking static clinical features was introduced by the NYU Medical Center. In this system a lesion is checked for Asymmetry, Border irregularity, Color variegation and Diameter. Diagnosis based on the clinical ABCD system has achieved a sensitivity of roughly 80%. This low sensitivity has led to the practice of removing almost any atypical mole. In addition, the ABCD system can only be applied to moles greater than 6 mm in diameter. It would be desirable to detect malignant moles at an even earlier stage.

In Great Britain, the Seven Point Checklist was introduced to improve the sensitivity of the clinical exam. In this method, three major features (change in size, shape or color) and four minor features (inflammation, crusting or bleeding, sensory change and diameter greater than 7 mm) are assessed. The inclusion of both static and dynamic change has led to a higher sensitivity in diagnosis. The emphasis on change in this method shows the dynamics of the lesion. However, the system has not gained wide acceptance because there have not been enough studies in order to quantify what rate of changes are considered alarming, since there are various rates of change which are acceptable and these rates may vary according to the individual. In addition, applications of this system have led to low specificity. Some of the parameters of the checklist are subjective, such as the sensory ones, and hence may not be repeatable, thus causing a problem in developing an objective diagnosis/monitoring system.

Photography has been used to aid in record keeping, but subtle changes in angle, lighting, skin tension and distance can affect the reading and therefore cause misdiagnosis. In addition, photographs, especially polaroids which are commonly used, can show color degradation over time. The newest methods of skin image tracking rely on epiluminescence microscopy (ELM). This technology looks deeper into the skin and is able to image structures up to the dermis-epidermis junction. In depth investigations have led to deduction of relevant features bearing a high correlation with malignancy. As the technique allows visualization of features not visible to the naked eye, using this technique results in higher sensitivity and specificity than that obtained with the clinical ABCD system. Typical values obtained with this method range from 92–100% for the sensitivity and 80–92% for specificity.

ELM, although better than previous techniques, has not yet been brought to the necessary level of sensitivity and specificity. There is a lack of exact correlation with structures seen in the histology. In current applications of epiluminescence microscopy technique the image capturing process involves pressing a transparent glass or plastic on the skin. This can introduce error into the system since different applications of pressure cause a different stretching of the skin which is imaged onto the camera. As there is no regulation of the pressure, the images captured are not fully repeatable. In addition, the other features by which the current ELM technology operates are extremely difficult to obtain in an automated way in a repeatable fashion. Various features which are important in the ELM are dynamic by nature and take some time before they develop. Therefore, findings may be misinterpreted due to lack of exact staging of the mole or external factors affecting the interpretation. Thus the interpretation of the features is somewhat difficult. In some systems, the lesion area is determined by manually selecting an appropriate threshold to determine the skin/lesion border. As all the parameters are then measured automatically based on this choice, the results may be biased and therefore not repeatable. Therefore, it is necessary to provide a robust system of parameters for use in diagnosis.

Other areas in which temporal comparison of skin surface images may be of use include cosmetics, skin treatment and identification. To this end a method of storing an image which is repeatable and comparable would be desirable.

Thus, it would be desirable to provide a fully automatic, sensitive, specific and cost-effective system for measurement and temporal tracking of lesion skin images which would be repeatable and comparable.

SUMMARY OF THE INVENTION

Accordingly, it is a principal object of the present invention to overcome the disadvantages associated with current ELM and clinical technology and to provide a method for temporal comparison of skin surface images which is fully automatic and based on robust parameters.

In accordance with a preferred embodiment of the present invention, there is provided an apparatus for temporal comparison of skin surface images comprising:

means for obtaining a digital image of a skin area and storing same for analysis and display;

means for determining in iterative fashion a region of interest within said digital image according to a set of predetermined image color parameters;

means for separating said region of interest into data values representing color clusters and color islands;

means for mapping said data values to be associated with respective skin and lesion data sets;

means for extracting from said respective data sets measurements corresponding to a set of predetermined image measurement parameters;

means for performing statistical calculations on said respective extracted data set measurements to obtain a set of numerical factors associated with predetermined image analysis categories;

means for storing said set of numerical factors;

means for analyzing said set of numerical factors for diagnosis determination; and means for displaying said digital image, said numerical factors and said diagnosis determination.

In a preferred embodiment of the invention, a CCD camera is provided with telecentric optics enabling the capture of images with constant magnification independent of the camera-object distance. Therefore, the sensitivity to height location of the camera above the object is markedly reduced. The measurement system is non-contact and non-destructive. The camera is linked to a PC with a frame grabber for storing the image and processing means for calibrating light and for calculating statistics of the image. The illumination source provides a homogeneous illumination of the skin. The light is calibrated by eliminating the effects of the illuminating light from the assumed white, spatially invariant light, and then correcting the acquired image of the lesion. A model has been provided which transforms an acquired image (AI) of an object into the model image (MI) which would have resulted if illumination of the object were solely by the reference (white) light.

Three monochromatic images are produced, one for each of three color channels. The three images are grabbed and processed, and a combination of these three images gives the true color (red, green and blue or RGB) image. The RGB image is then transformed to the CIE-Lab representation. An algorithm uses the image and reference image to calculate the skin/lesion border which the eye would suggest if the lesion was illuminated by a standard white light. It separates the image into two parts, the largest lesion and the rest of the skin. The image is processed to give the contour of the lesion, and statistics are extracted to score the necessary parameters (metrics). The algorithm may operate on both clinical images or ELM images. The algorithm is fully automatic and needs no human intervention. In addition, processing means for comparing more than one image are provided.

Therefore, the physician is provided with various metrics in a more reliable fashion than could be done manually and these are displayed together with the images obtained at various times. The images can be examined for visual changes over time and for quantitative change in the metrics over time.

The present invention provides a comprehensive solution to the problems encountered in previous lesion tracking systems. A system is provided to assist the physician in the decision making process of malignancy determination. A skin lesion border is extracted which corresponds to the human perception. Fully automatic extraction of the ABCD parameters and others from both clinical and ELM images is accomplished through a scoring system which helps the physician determine benign/tumerous nevi and their type. The features are extracted in a manner which is fairly immune to noise, i.e. robust, thus leading to a high repeatability and reliability of the system. The features extracted have a high correlation with the malignancy of the lesion enabling the physician to make a decision regarding the type of lesion with high specificity and sensitivity.

Other features and advantages of the invention will become apparent from the following drawings and description.

BRIEF DESCRIPTION OF THE DRAWINGS

For a better understanding of the invention, with regard to the embodiments thereof, reference is made to the accompanying drawings, in which like numerals designate corresponding elements or sections throughout, and in which.

DETAILED DESCRIPTION OF A PREFERRED EMBODIMENT

Figure 1:
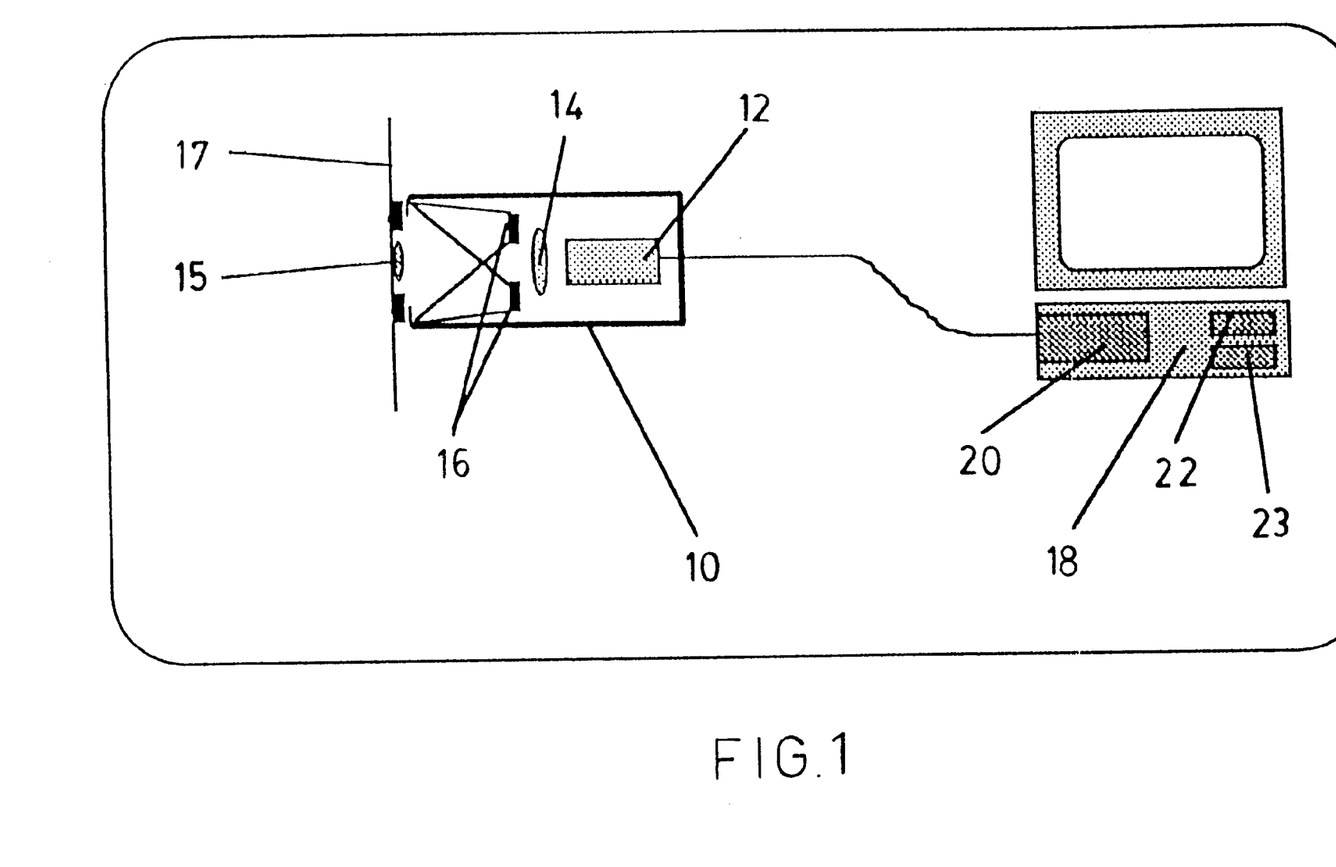
FIG. 1 is a schematic block diagram of a system for skin surface image tracking constructed and operated in accordance with the principles of the present invention.

Referring now to FIG. 1, there is shown a schematic block diagram of an apparatus for measurement and temporal comparison of skin surface images 10 constructed and operated in accordance with the principles of the present invention. Apparatus 10 comprises a CCD camera 12 equipped with telecentric optics system 14. Telecentric optics system 14 provides a non-contact measuring system with a constant focus which is able to capture the image of the lesion 15 with constant magnification even under various skin-camera distances due to its large depth of field. An illumination source 6 is used for illumination of the skin 17. Camera 12 is connected to feed input to computer processer 18 (minimum requirements for the computer are: Pentium 133 Mhz, 32 MB RAM and 1 Gigabyte hard disk) which is equipped with a frame grabber 20 and hard disks 22, 23.

This configuration enables the health care professional to operate the system to obtain reliable diagnoses based on not only the current parameters extracted but also on the rate of change of these parameters over time. The inventive system is simple to operate and can be operated by a technician.

Figure 2:
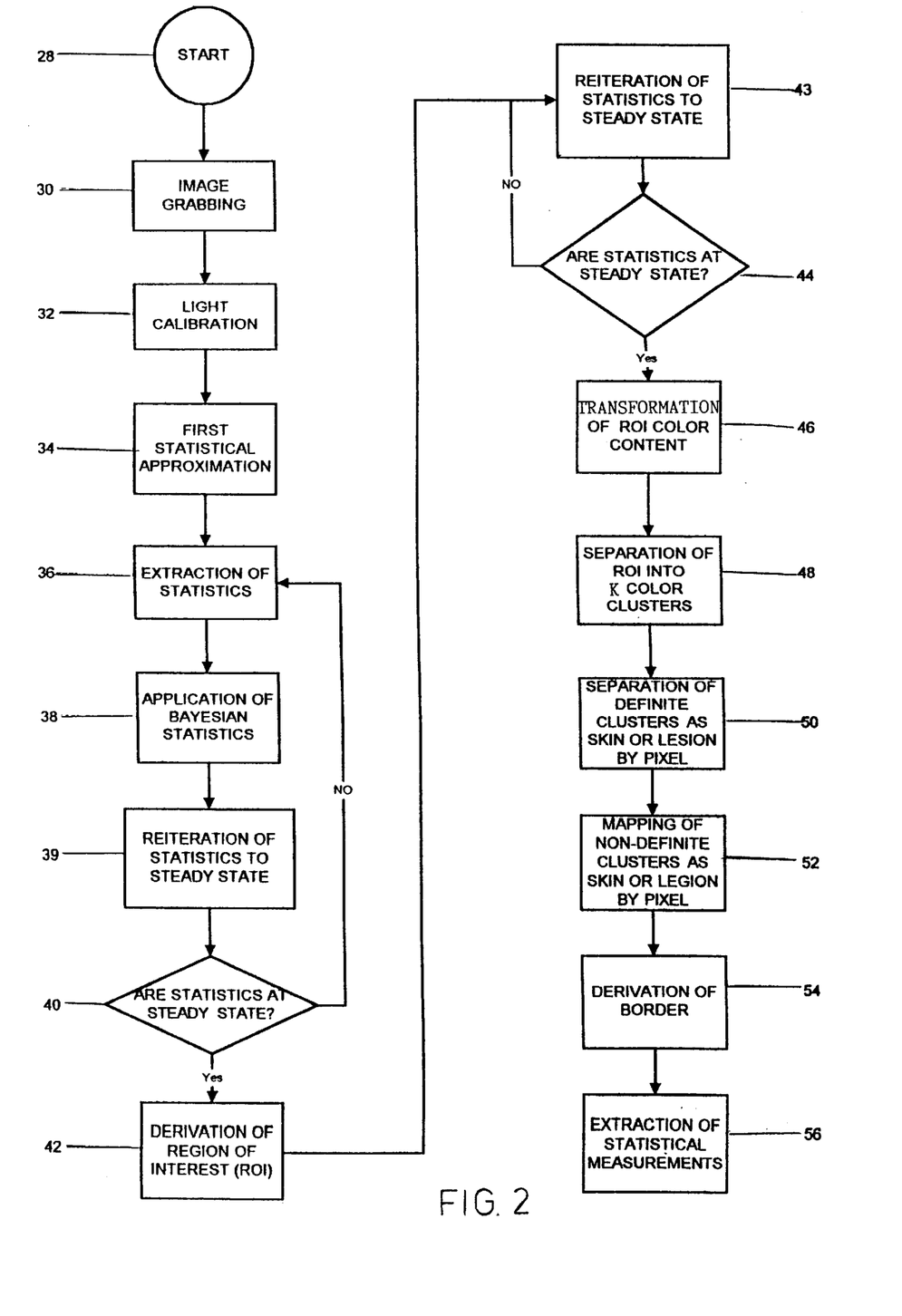
FIG. 2 shows a flowchart for extracting the statistical parameters of interest.

In FIG. 2 there is shown a flowchart representing the operation of computer processor 18 in calculating the desired parameters for diagnosis. After initialization in start block 28, the image is grabbed in RGB format in the first block 30. Subsequently, in block 32, the light is calibrated. This is the process of modifying the acquired image of the lesion and emulating illumination of the lesion by a spatially constant, time invariant, white reference light source. In order to eliminate the effects of illuminating light (IL) variability, the difference in the illuminating light from the reference light is recorded and the acquired image of the lesion is corrected accordingly. In order to do this, a model is needed to transform the acquired.image (AI) of the object illuminated by the illuminating light, to the model image (MI) which would have resulted if the illumination of the object was by a white reference light (RL). Assuming the color is given by the RGB components, and the camera provides a linear sensitivity to color intensity and is noiseless, the transformation is:

$$MI\{R,G,B\}=AI\{R,G,B\}*RL\{R,G,B\}/IL\{R,G,B\} \quad (1)$$

This transformation is applied for every pixel in space, thus correcting for the $\{R,G,B\}$ spatial variance of the illuminating light.

However, the camera is neither linear nor noiseless. Assuming a small additive uncorrelated Gaussian noise (GN) in each of the color components in the camera, a more correct model is:

$$MI\{R, G, B\} = \frac{(AI\{R, G, B\} - GN\{R, G, B\})*(RL\{R, G, B\} - GN\{R, G, B\})}{IL\{R, G, B\} - GN\{R, G, B\}} + GN\{R, G, B\} \quad (2)$$

In order to obtain estimates of the Mean Camera Noise the image is obtained several times with no illumination, and the results are averaged.

In order to account for the non-linearity of the camera, a look-up table is provided for each of the three color components. This look-up table is defined by illuminating a multiplicity of distinct color samples, grabbing and extracting the actual Ra, Ga and Ba values and inserting in the look-up table the desired Rd, Gd and Bd values. For missing values extrapolation and interpolation are employed.

In block 34 a first approximation of the skin statistics is derived, from which a first approximation of the skin/lesion location is derived. This is termed segmentation. In the segmentation process a narrow strip around the periphery of the image is defined from which the color statistics (mean and standard deviation) are extracted. These are the initial approximation skin statistics. Then any pixel whose RGB values are within a predetermined number of sigmas from the skin statistics is classified as skin, otherwise it is classified as lesion. The predetermination of the number of sigmas is derived from statistical hypothesis testing methods.

Based on the approximate segmentation, skin/lesion statistics are derived in block 36. Now that all pixels have been classified as belonging to skin or lesion, the color statistics of the skin and lesion are extracted from all pixels classified as skin or lesion, respectively.

Using the above skin/lesion statistics, Bayesian decisions can be used to extract a more advanced approximate segmentation in block 38. Each pixel's distance from both the skin and lesion is calculated in accordance with Bayesian statistics taking into account mean and standard deviations of the color components. Then the pixel is classified as belonging to either the skin area or the lesion area by determining the shortest distance which is between them (multiplied by a safety factor). These calculations are reiterated in block 39.

In decision block 40 the statistics are reiterated until steady-state is reached. This involves repeating blocks 36, 38 and 39. With this information, in block 42 the Region of Interest (ROI) is derived. The ROI is a slightly larger section than the advanced approximation of the lesion derived earlier. All further operations and calculations are based on the ROI. The statistics are again reiterated in block 43 and in decision block 44 the statistics are checked to see if they are at steady state. If not, block 43 is repeated until steady state is reached for the ROI.

Figure 3:
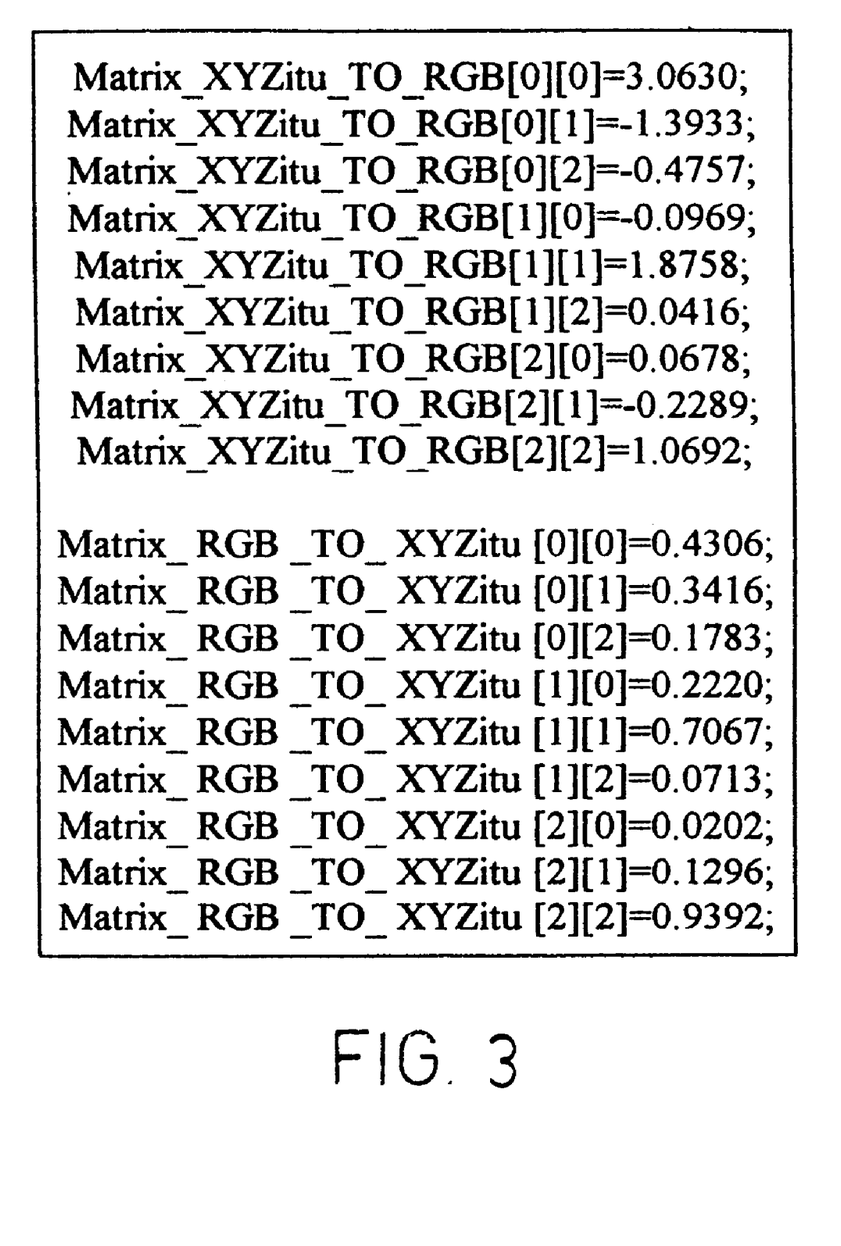
FIGS. 3a–b show respectively a matrix of values for transformation of the RGB representation to the CIE-Lab representation and the reverse transformation.

Once steady state has been reached, in block 46 each pixel from the ROI is transformed via a mathematical non-linear transformation from its RGB representation to its CIE-Lab representation according to the table in FIG. 3. The CIE-Lab representation is consistent with Equal perception, i.e. the distance that humans perceive between any two colors in this representation is proportional to the Euclidean distance between them, and this is what is represented in the CIE-Lab space. This does not hold true for the RGB representation.

Next, in block 48, the ROI is separated into color clusters by the well known Kmeans algorithm. Initializations of the algorithm are derived from ROI skin and lesion statistics extracted earlier. The number of clusters (K) is determined fully automatically by an iterative procedure on the Kmeans algorithm for splitting the clusters based on variance of the individual color clusters.

Initially, in block 50, clusters which definitely belong to skin or lesion are extracted. This decision is based on color proximity to the a priori skin/lesion color estimates, the physical size of the part of each color cluster residing in the a priori assumed skin or lesion area (i.e. how many pixels out of the specific cluster reside in the a priori assumed skin or lesion area) and the distance of the physical center of the color cluster from the center of the a priori approximation of the lesion. Based on these metrics a score is calculated for each cluster, for its probability to be a skin cluster and for its probability to be a lesion cluster. Then, starting from the clusters having the highest score for either the skin or the lesion, clusters are consecutively assigned to be a definite skin or lesion cluster, until a certain fraction of the a priori lesion and skin area is accounted for by definite clusters.

Following this, in block 52, all ROI image points belonging to clusters which were not established to be either definitely skin or definitely lesion are remapped to belong to clusters which were mapped definitely. The mapping is based on probabilistic color proximity. The color distance of every pixel of all clusters which are not definitely mapped from both lesion and skin is calculated. The distance from the lesion or skin is the distance of that pixel from the closest definitely mapped color cluster of the lesion or skin. Then, based on the skin and lesion distances a decision is made whether this pixel belongs to the skin or lesion. The decision is not deterministic, it is probabilistic, i.e. the smaller the distance the higher the likelihood of the pixel being mapped to that definitely mapped cluster. This method of decision is more robust than deterministic based decisions.

In block 54 the skin/lesion section, and hence the border, is derived. All the pixels belonging to clusters which were mapped as skin are labelled as skin, all the rest being lesion. A binary image is built where every image point belonging to the skin clusters is given a HI value and all image points belonging to lesion clusters are given a LOW value. After performing morphological operations on the binary image in order to eliminate the effect of hairs, the border is those pixels where the derivative of the binary image value is maximal.

In final block 56 statistical measures are extracted, as well as the ABCD system metrics. These measures are standard parameters which are calculated by custom software:

Area (Ar) is calculated by the number of pixels contained in the lesion area as determined in block 54.

Asymmetry (A) is evaluated for each of the RGB colors, with perpendicular axes chosen in such a way that one of the axes is parallel with the primary axis (PAX) of the lesion (in the direction of the principle angle (PA)) and the origin is at the center of gravity (COG) of the lesion. The center of gravity of the lesion is determined by averaging the centroids obtained for each individual color component. The principle angle is the angle of an axis passing through the centroid of an image, at which the moment of inertia (INT) is minimized. The PAX is the axis with this angle. The SAX (secondary axis) is an axis at 90° to the PAX. The moment of inertia is the sum of inertias of each individual color component.

The formula for asymmetry should be zero for a lesion symmetrical about both the PAX and the SAX. A lesion which is symmetrical about one of the axes would have an asymmetry value of MAX ASYMM/2. A lesion which is quite asymmetrical would have an asymmetry value of MAX ASYMM. If the maximum inertia possible is (MAX INT PAX {R,G,B} and MAX INT SAX {R,G,B}) then asymmetry is given by:

$$\text{Asym}=\text{sqrt }(\text{SAX Asym}^2+\text{PAX Asym}^2) \quad (3)$$

where $$\text{SAX Asym}=\min\,(\text{sqrt }((\text{SAX Asym R}^2+\text{SAX Asym G}^2+\text{SAX Asym B}^2)/3,\text{MAX ASYMM}/2) \quad (4)$$

and $$\text{PAX Asym}=\min\,(\text{sqrt }((\text{PAX Asym R}^2+\text{PAX Asym G}^2+\text{PAX Asym B}^2)/3,\text{MAX ASYMM}/2) \quad (5)$$

and $$\text{PAX Asym }i=(5^*\text{ Inertia (PA) }i/\text{MAX INT PAX }i) \quad (6)$$

$$\text{SAX Asym }i=(5^*\text{ Inertia (PA) }i/\text{MAX INT SAX I}) \quad (7)$$

where i=R, G, or B.

Border irregularity, (the notching and scalloping of the contour of the skin/lesion border) is evaluated via the formula:

$$B=P^2/4\pi A \quad (8)$$

where P is the perimeter of the border and A is the area of the lesion bounded by the border.

Color variegation refers to lesions with shades of dark brown, tan, light brown, red white, blue, black and combinations thereof. It is necessary to know the number of distinct colors of interest existing in a given lesion. To this end, the color information is compiled providing a list for each color above of distinct color islands whose size is greater than some predetermined size. Colors are determined according to the standards of the National Bureau of Standards. In addition, the number of such islands is determined.

The color variegation metric C is calculated as the length in the CIE-Lab color space of the shortest contour connecting all of the color clusters describing the lesion.

The diameter metric D is calculated as the maximal diameter of the lesion.

In FIG. 3 two matrices are defined, each with three rows and columns where the first index refers to the row and the second to the column. Having defined these matrices we define the vector Ref via:

$$\text{Ref}=\text{Matrix\_RGB\_TO\_XYZitu}^*\text{RefRGB} \quad (9)$$

where RefRGB is a column vector whose values are:

$$\text{RefRGB}[0]=\text{RefRGB}[1]=\text{RefRGB}[2]=255 \quad (10)$$

and * denotes vector multiplication. Let Xn=Ref[0], Yn=Ref[1], Zn=Ref[2]. Also pow(x,y) is defined to mean x to the power of y.

In order to transform RGB color representations to the CIE-Lab representation, the R, G, B values of a given color are defined by:

vec1[0]=R, vec1[1]=G, vec1[2]=B. Then with vec=Matrix_RGB_TO_XYZitu*vec1; and setting X=vec[0], Y=vec[1] and Z=vec[2], we have $$L=116^*\text{pow}((Y/Yn),\text{THIRD})-16,0.0) \quad (11)$$

$$a=500^*(\text{pow}((X/Xn),\text{THIRD})-\text{pow}((Y/Yn),\text{THIRD})) \quad (12)$$

$$b=200^*(\text{pow}((Y/Yn),\text{THIRD})-\text{pow}((Z/Zn),\text{THIRD})) \quad (13)$$

In order to transform from CIE-Lab back to RGB, compute $$\text{vec1}[0]=L/116.0+a/500.0 \quad (14)$$

$$\text{vec1}[1]=L/116.0 \quad (15)$$

$$\text{vec1}[2]=L/116.0-b/200.0 \quad (16)$$

and $$fp[i]=\text{pow}((\text{vec1}[i]+16.0/116.0),3.0)\text{ for I}=0,1,2 \quad (17)$$

Then compute:

$$X=Xn^*fp[0] \quad (18)$$

$$Y=Yn^*fp[1] \quad (19)$$

$$Z=Zn^*fp[2] \quad (20)$$

Letting vec[0]=X, vec[1]=Y, vec[2]=z one obtains $$\text{vec3}=\text{Matrix\_XYZitu\_TO\_RGB}^*\text{vec} \quad (21)$$

where R=vec3[0], G=vec3[1] and b=vec3[2] is the desired result.

Figure 4:
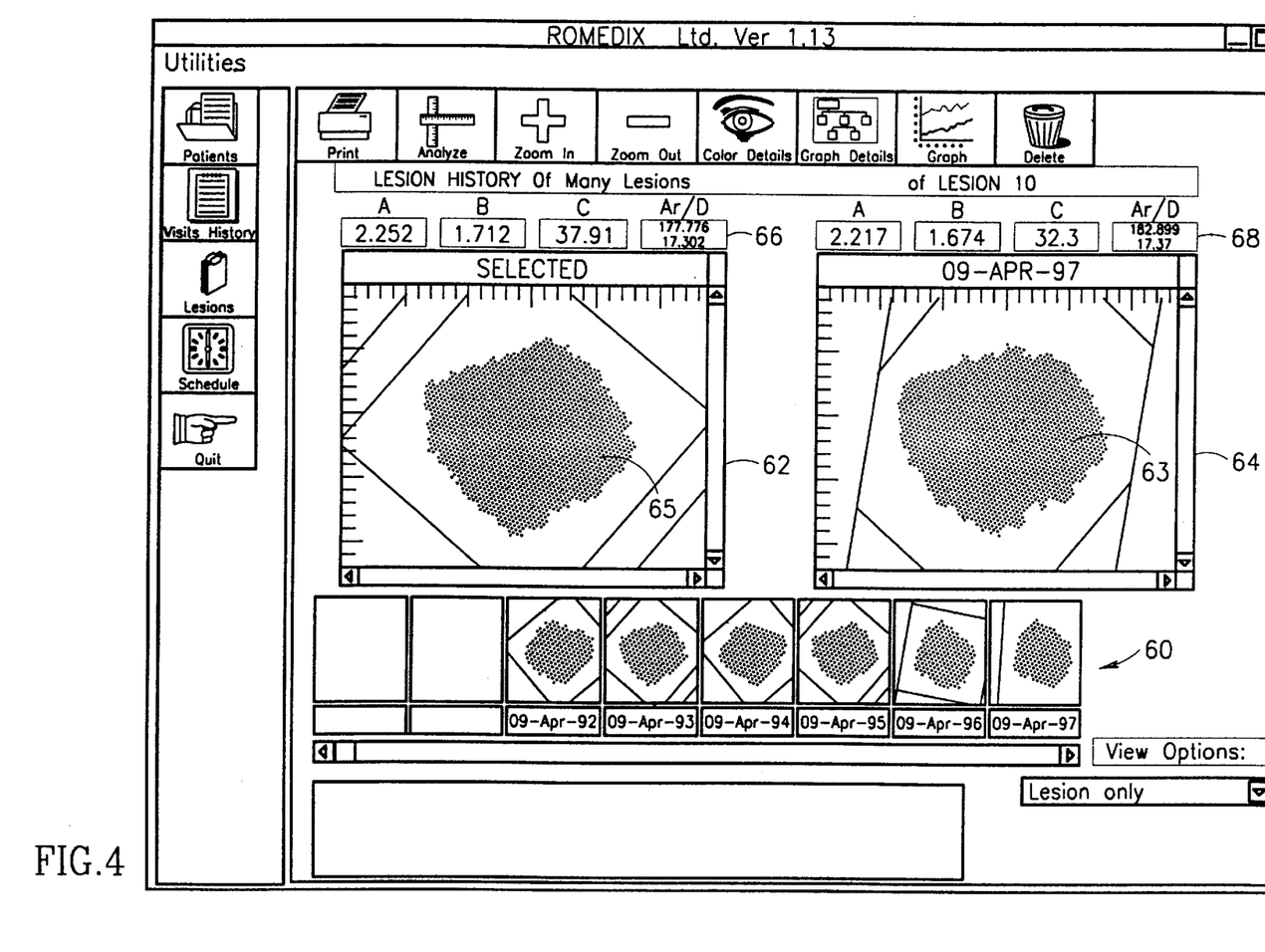
FIG. 4 is a display screen showing the current skin surface image as compared to a selected previous one at high resolution.

FIG. 4 shows the display screen as viewed by the user, in which, by way of example, a patient's file has been shown, with six images of a specific lesion. The six lesion images are shown at low resolution in lower window 60. All lesion images are aligned and oriented in parallel automatically by the software, so that the physician does not have to trouble himself in capturing the image in the same orientation as the previous time. Any pair of images of the same lesion can be selected to be displayed one next to the other in a high resolution scale, in upper large windows 62 and 64. In this example, the physician has selected one previous lesion image 63 to compare with current lesion image 65 at high resolution in larger windows 62 and 64 respectively. Above each larger window the physician is provided with (A,B,C, D,Ar) metrics 66 and 68 of the lesion as determined from the respective lesion images 62 and 64.

Figure 5:
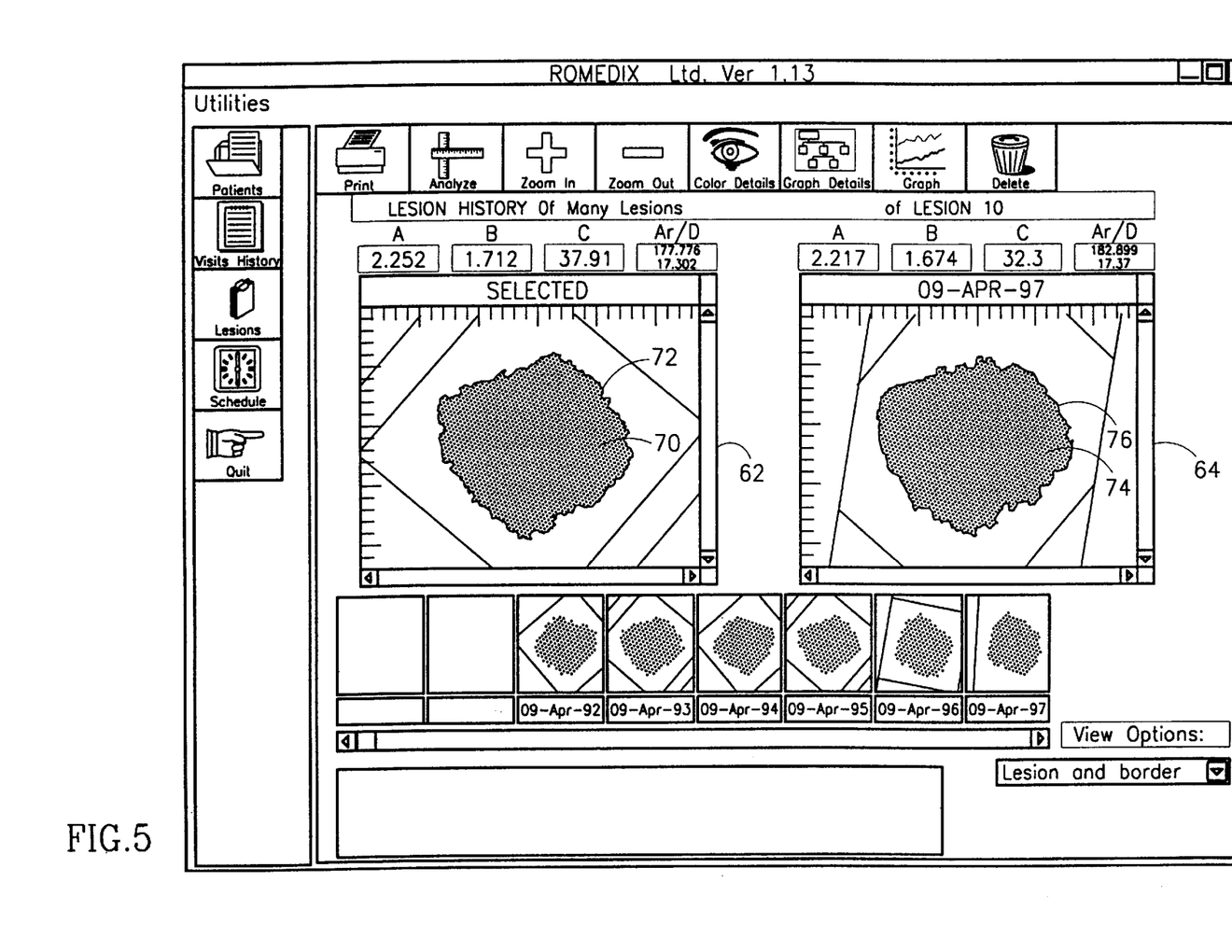
FIG. 5 is a display screen showing the images with the automatically extracted border highlighted.

In FIG. 5 the user has chosen the option of viewing both lesion image 70 and border 72 as determined by the algorithm in the larger windows 62 and 64. This allows display of both the current lesion image 70 in window 62 and a previous lesion image 74 in window 64 at high resolution with automatically extracted borders 72 and 76 highlighted. The physician may also display both borders on the same lesion image (either current or previous) overlayed, in order to see subtle differences between the borders. Since the images are automatically centralized and oriented in parallel, this is not a problem.

Figure 6:
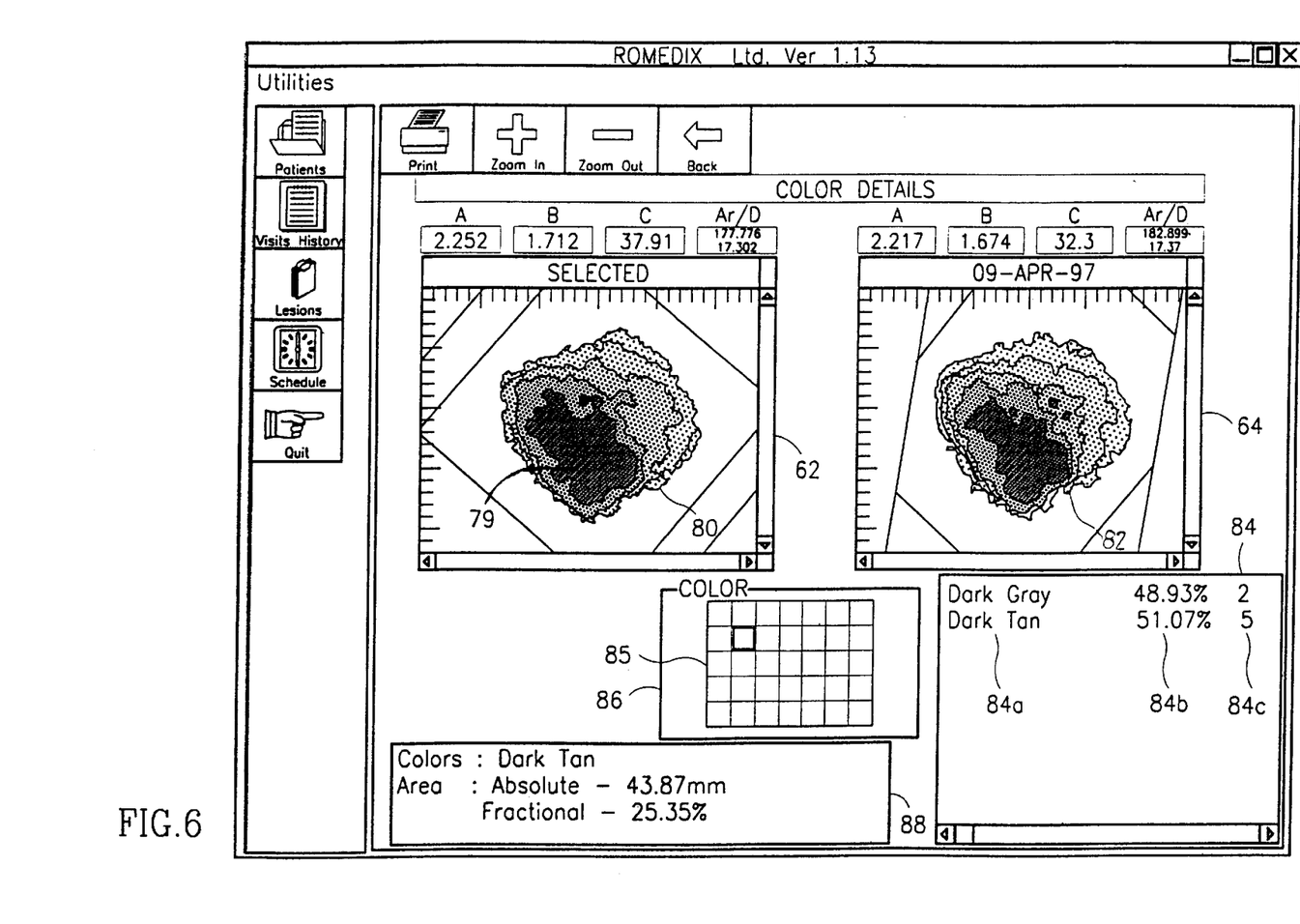
FIG. 6 is a display screen showing an image comparison of the color variegation of two images composed of various color islands.

In FIG. 6 the physician has chosen the color details module where the various changes in the color components composing the lesion image are examined. Two lesion images 80 and 82 are selected at high resolution in windows 62 and 64, respectively. In window 84, the names of all color clusters appearing in the image (84a) are printed alongside the fractional area they account for in the lesion (84b) and the number of color islands in the lesion with that specific color cluster (84c). Selecting any pixel within the lesion image (e.g. 79) yields the color cluster name of the color island that the specific pixel belongs to and the area of that color island as displayed in windows 86 and 88. Color islands of a given color cluster are those topologically disjointed areas belonging to the given color cluster. In window 86 there is shown color chart 85 with various colors displayed. Highlighted in color chart 85 is the color closest to the specific color island to which the selected pixel belongs. In parallel, in window 88 information is shown on the selected pixel, including the name of the color island to which it belongs, the area of the color island to which it belongs, and the fractional area of that color island out of the total lesion area.

Figure 7:
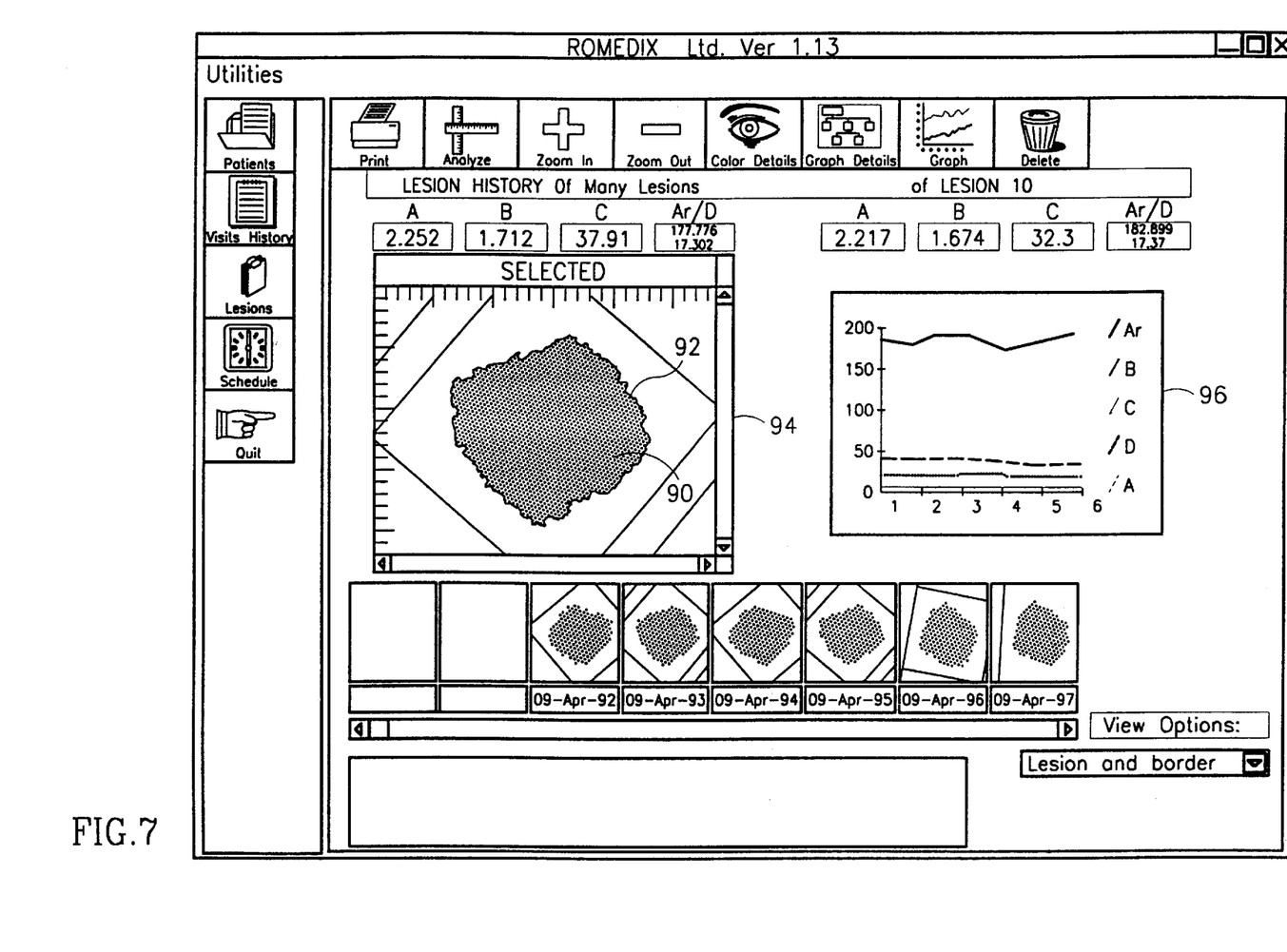
FIG. 7 shows a graph of various automatically extracted metrics of the displayed selected image over a course of time.

FIG. 7 shows a selected lesion image 90 and border 92 displayed in window 94 with all of the calculated metrics graphed as a finction of time in window 96. The x-coordinate is time and the y-coordinate is the value of the specific metric at time x. This allows the physician to track the evolution of lesion metrics over the course of time and note changes.

Figure 8:
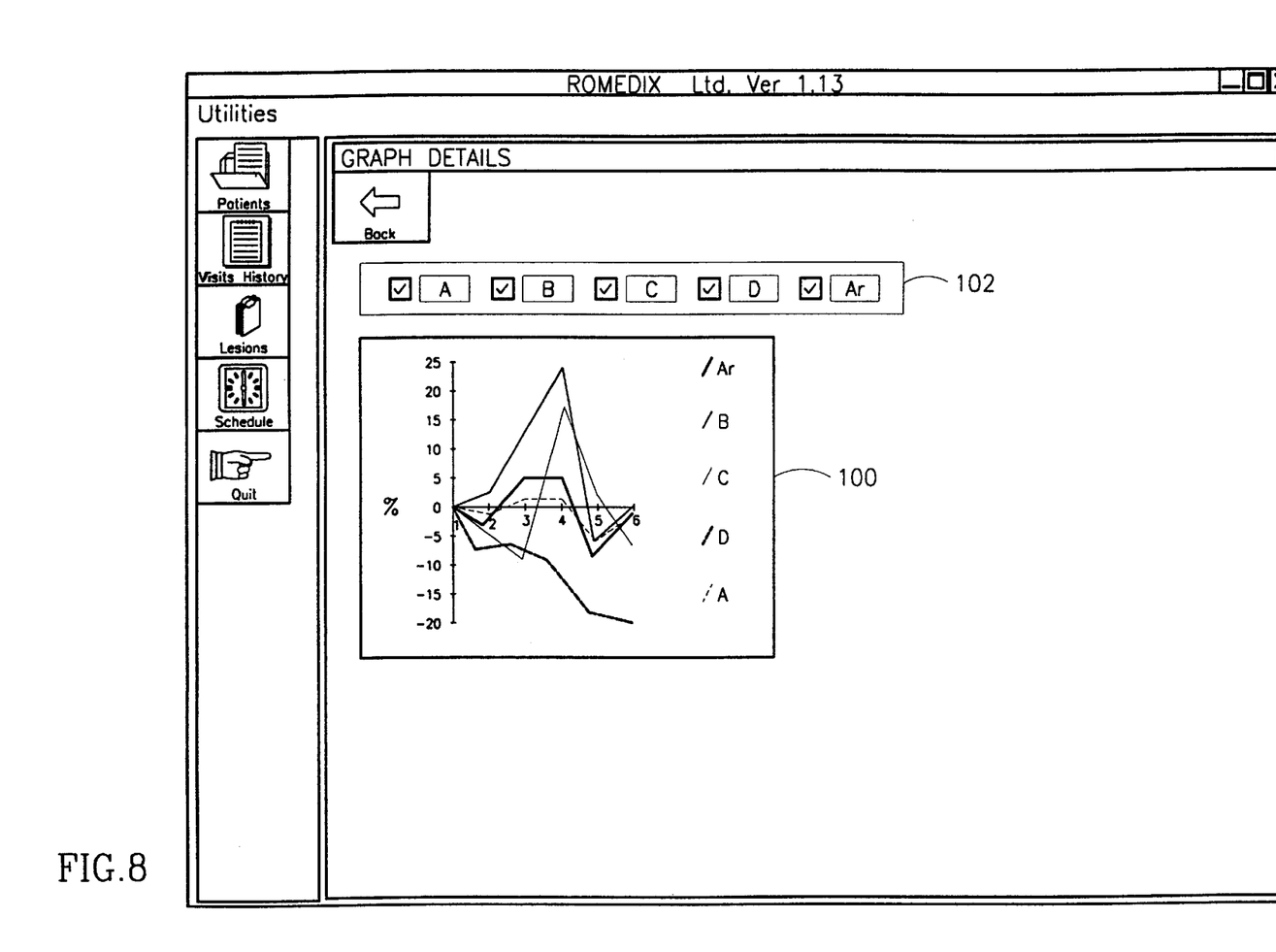
FIG. 8 shows a graph of the percent change in the various automatically extracted metrics over a course of time.

In FIG. 8 the user has chosen the option of Graph Details to show the quantitative change in time of the various metrics in finer detail. In graph 100 the value plotted on the y axis is the percentage change in each specific parameter's value from the value of that specific parameter at the first visit. The changes in all clinically measured and computed parameters can be graphed independently or simultaneously in order to correlate changes in one parameter with another. In window 102 the user has chosen the parameters desired to be displayed in graph 100.

In summary, the inventive skin surface imaging system provides the physician with an invaluable tool to assist in assessing cancerous dynamics of a lesion and hence a tool to simplify and make more objective the decision regarding the malignancy of a lesion.

Having described the invention with regard to specific embodiments thereof, it is to be understood that the description is not meant as a limitation, since further modifications may now suggest themselves to those skilled in the art, and it is intended to cover such modifications as fall with in the scope of the appended claims.

We claim:

1. A method of analysis and temporal comparison of skin surface images comprising the steps of:
   obtaining a digital image representing physical aspects of a skin area and storing same for analysis and display;
   processing said digital image representing said physical aspects for determination of a diagnostic data structure comprising the steps of:
      determining in iterative fashion a region of interest of skin color variations within said digital image according to a set of predetermined image color parameters;
      separating said skin color region of interest into color clusters and color islands represented by data values associated with said digital image;
      mapping said data values associated with said digital image into respective ones of skin and lesion data sets;
      extracting metrics from each of said respective skin and lesion data sets, said metrics corresponding to a set of skin surface image diagnostic categories;
      performing statistical calculations on said respective extracted data set metrics to obtain a diagnostic data structure associated with said predetermined skin surface image diagnostic categories;
      storing said diagnostic data structure; and
   displaying said digital image and said diagnostic data structure relating to said physical aspects for use in a diagnostic determination.

2. The method of claim 1 further comprising the step of comparing said digital image information and said diagnostic data structure of said image with a second, previously obtained image and a diagnostic data structure of said second image.

3. The method of claim 1 further comprising the step of automatically centralizing and orienting in parallel at least two of said images.

4. The method of claim 1 wherein said step of obtaining a digital image comprises the steps of grabbing said digital image and calibrating a light to eliminate the effects of illuminating light on said image.

5. The method of claim 1 wherein said step of mapping comprises the steps of:
   scoring said color clusters with respect to skin-lesion values;
   determining those color clusters which definitely belong to said skin and lesion data sets according to said skin-lesion values; and
   assigning those color clusters whose skin-lesion values are of a predetermined intermediate range of skin-lesion values to belong to said respective skin and lesion data sets according to statistical probability using said skin-lesion values and a distance value from said points corresponding to said lesion values as a reference.

6. The method of claim 1 wherein said step of displaying said digital image comprises displaying said image with an extracted border superimposed thereon.

7. The method of claim 1 wherein morphological operations are performed on said extracted border to eliminate the effect of hairs on said extracted border.

8. The method of claim 1 wherein said step of displaying said digital image comprises displaying said image alongside at least one stored, previously obtained image.

9. The method of claim 1 wherein said step of displaying said digital image comprises displaying said image with borders extracted from at least two images superimposed thereon.

10. The method of claim 1 wherein said step of displaying said digital image comprises displaying said color islands on said image.

11. The method of claim 1 wherein said step of displaying said digital image comprises displaying the color name of said color islands according to a predetermined set of standards and displaying an area of said color islands.

12. The method of claim 1 wherein said step of displaying said diagnostic data structure comprises creating a graph of at least one of said metrics over time.

13. The method of claim 1 wherein said step of displaying said diagnostic data structure comprises creating a graph of percent change in at least one of said metrics extracted from at least two images.

14. An apparatus for analysis and temporal comparison of skin surface images comprising:

means for obtaining a digital image representing physical aspects of a skin area and storing same for analysis and display;

processing means for processing said digital image representing said physical aspects for determination of a diagnostic data structure comprising:

means for determining in iterative fashion a region of interest of skin color variations within said digital image according to a set of predetermined image color parameters;

means for separating said skin color region of interest into color clusters and color islands represented by data values associated with said digital image;

means for mapping said data values associated with said digital image into respective ones of skin and lesion data sets;

means for extracting metrics from each of said respective skin and lesion data sets, said metrics corresponding to a set of skin surface image diagnostic categories;

means for performing statistical calculations on said respective extracted data set metrics to obtain a diagnostic data structure associated with said predetermined skin surface image diagnostic categories;

means for storing said diagnostic data structure; and means for displaying said digital image and said diagnostic data structure relating to said physical aspects for use in a diagnostic determination.

15. The apparatus of claim 14 wherein said means for obtaining a digital image comprises a CCD camera equipped with telecentric optics allowing image acquisition independent of the camera-object distance.

16. The apparatus of claim 14 in which said diagnostic data structure includes data for determining a lesion border for said image, said lesion border being displayed in superimposed fashion on said image.

* * * * *